US012539398B2

(12) United States Patent
Grandolfo et al.

(10) Patent No.: US 12,539,398 B2
(45) Date of Patent: Feb. 3, 2026

(54) EXTERNAL END DEVICE EQUIPPED WITH A TISSUE-INGROWTH CUFF

(71) Applicants: Nicola Grandolfo, Triggiano (IT); Emilio Magaldi, San Mango Piemonte (IT)

(72) Inventors: Nicola Grandolfo, Triggiano (IT); Emilio Magaldi, San Mango Piemonte (IT)

( * ) Notice: Subject to any disclaimer, the term of this patent is extended or adjusted under 35 U.S.C. 154(b) by 765 days.

(21) Appl. No.: 17/758,878

(22) PCT Filed: Jan. 13, 2021

(86) PCT No.: PCT/IB2021/050231
§ 371 (c)(1),
(2) Date: Jul. 14, 2022

(87) PCT Pub. No.: WO2021/144715
PCT Pub. Date: Jul. 22, 2021

(65) Prior Publication Data

US 2023/0033670 A1 Feb. 2, 2023

(30) Foreign Application Priority Data

Jan. 14, 2020 (IT) ........................ 102020000000577

(51) Int. Cl.
*A61M 25/04* (2006.01)
*A61M 25/01* (2006.01)

(52) U.S. Cl.
CPC ........ *A61M 25/04* (2013.01); *A61M 25/0194* (2013.01); *A61M 2205/04* (2013.01)

(58) Field of Classification Search
CPC ... A61M 39/00–39/0693; A61M 39/10–39/18; A61M 2205/04; A61M 1/159; A61M 1/14–1/387; A61M 39/391; A61M 39/0247; A61M 5/1408; A61M 25/0097; A61M 25/0028; A61M 25/02; A61M 25/04; A61M 25/0194; A61M 2025/0233; A61M 2025/0246; A61M 2025/0286; A61M 1/285; A61M 1/3661
See application file for complete search history.

(56) References Cited

U.S. PATENT DOCUMENTS 8,870,825 B2 * 10/2014 Grandolfo ........... A61M 1/3659 604/175
2007/0078478 A1 4/2007 Atkins et al.
2008/0312599 A1 12/2008 Rosenberg
(Continued)

FOREIGN PATENT DOCUMENTS

WO WO-2010146614 A2 * 12/2010 .......... A61M 1/3653
WO WO-2013108280 A2 * 7/2013 .......... A61M 1/3653

*Primary Examiner* — Cris L. Rodriguez
(74) *Attorney, Agent, or Firm* — FisherBroyles, LLP; Roger L. Browdy; Ronni S. Jillions

(57) ABSTRACT

An external end device has a casing, including a base, in which a distal opening is formed which receives a funnel-shaped septum having a tube trunk. Inside the tube trunk, the catheter is connected to the distal section of the fitting. A tubular coating has a proximal end adapted to be grafted onto the tube trunk and a distal end coaxially adhering to the catheter. A pair of bands of tissue-ingrowth material is fixed on the tubular coating, and an anchor ring, equipped with anchoring means, is sandwiched between the bands.

6 Claims, 3 Drawing Sheets

(56) References Cited

U.S. PATENT DOCUMENTS

| | | | | |
|---|---|---|---|---|
| 2010/0241084 | A1 | 9/2010 | Rosenberg | |
| 2012/0089096 | A1 | 4/2012 | Grandolfo | |
| 2012/0157926 | A1 | 6/2012 | Rosenberg | |
| 2012/0209206 | A1 | 8/2012 | Scandone, Jr. | |
| 2015/0051536 | A1* | 2/2015 | Mendels | A61M 1/3659 604/246 |
| 2015/0080804 | A1 | 3/2015 | Rosenberg | |
| 2018/0344984 | A1 | 12/2018 | Rosenberg | |
| 2020/0368496 | A1* | 11/2020 | Loesener | A61M 25/0097 |

* cited by examiner

Fig. 3
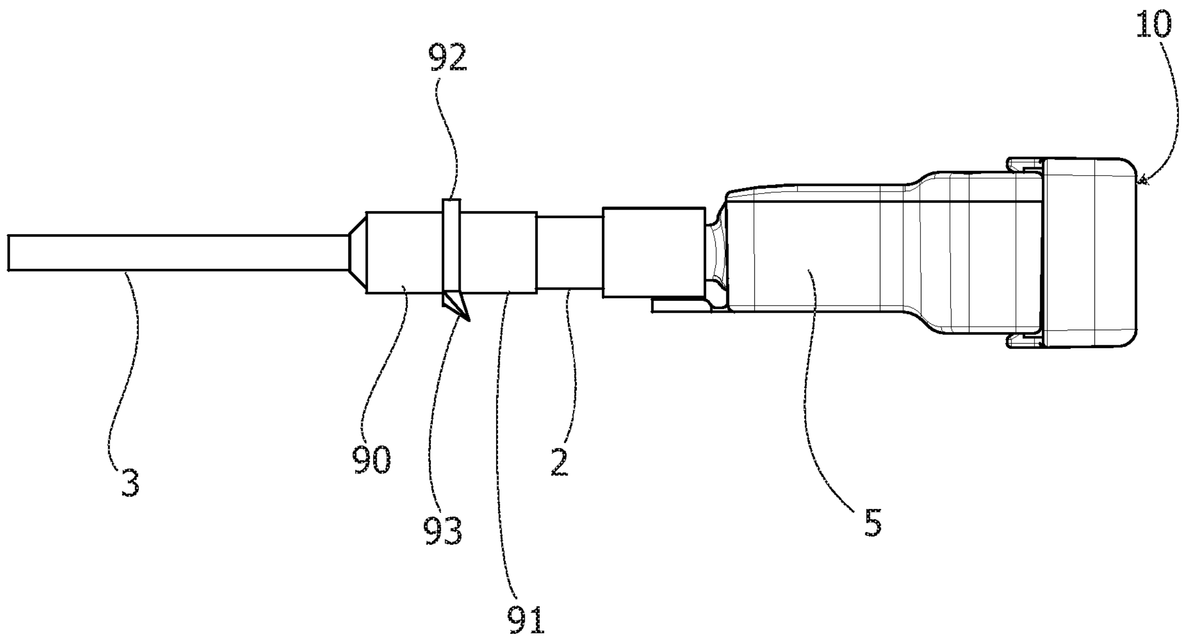
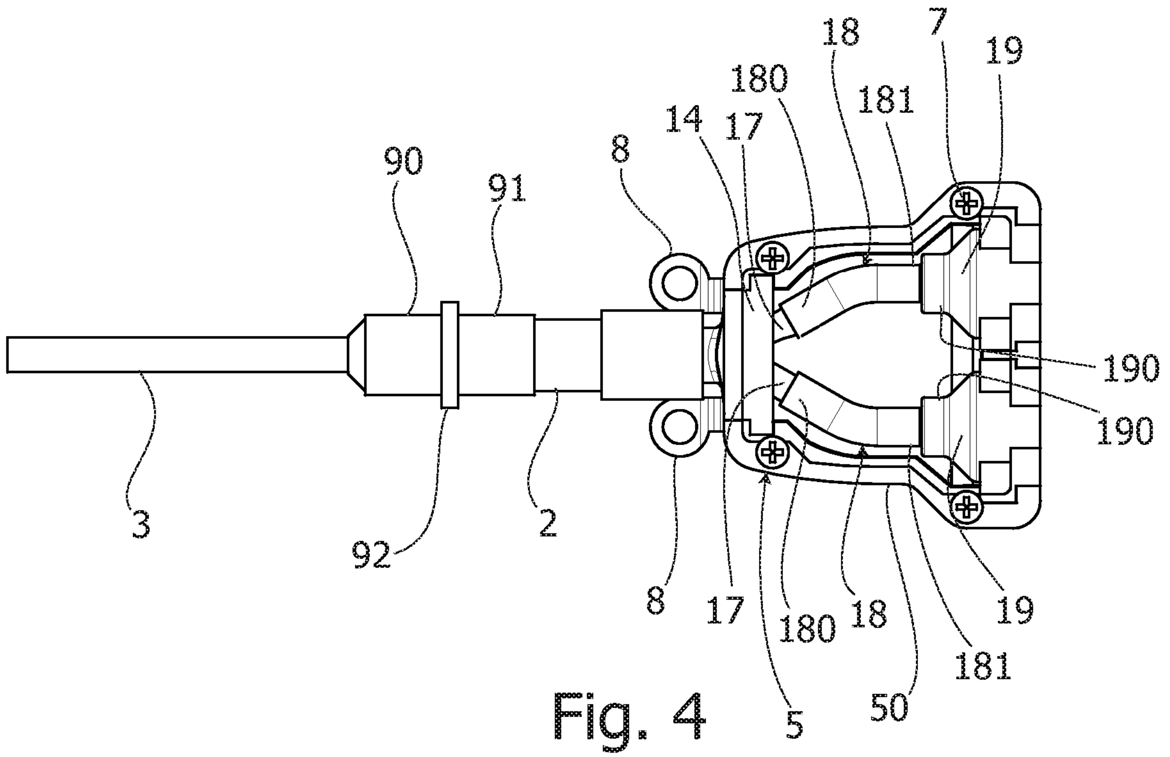
Fig. 4

EXTERNAL END DEVICE EQUIPPED WITH A TISSUE-INGROWTH CUFF

TECHNICAL FIELD

The present invention relates to an external end device usable, for example, in hemodialysis, peritoneal dialysis and chemotherapy. The external end device is equipped with a tissue-ingrowth cuff.

BACKGROUND ART

The current cuffs, positioned on permanent central venous catheters, consist of a Dacron band, glued on the catheter itself, and have a mechanical function and a biological function.

From the mechanical point of view, these cuffs, generally a ring-shaped pad, are made of a material foreign to the body. When positioned in the subcutaneous tissue, the cuffs are incorporated in the body, even if a reaction is generated that tends to isolate them from the surrounding tissues. The result is the formation of scar tissue which, penetrating into the filaments of the Dacron itself, effectively blocks it in that position, obtaining, as a final result, an adhesion that holds the cuff in place, preventing it from sliding outwards and therefore avoiding an accidental expulsion of the catheter itself. From the biological point of view, this scar tissue, at the same time, forms a sort of barrier to the progression, along the subcutaneous tunnel in which the catheter lies, of bacterial colonies which, inevitably, would reach the part of the catheter immersed in the blood and cause infections, at first localized and, subsequently, generalized.

All this, however, is very limited by the small size of the cuffs, which, in the known art, are generally not very wide. Their small width also causes that, with time passing, due to nurse care on patients using these catheters, the formation of scar tissue, little by little, yields, losing its mechanical function, with consequent release of the catheter and expulsion of the same.

US 2012/0209206 A1 discloses a tissue-ingrowth cuff for stabilizing an implanted catheter against movement. The cuff is actuated by a surgeon once moved to its desired location, to grip the catheter. The cuff comprises two body portions that are separately slidable along the catheter prior to coupling, but can be attached to each other around the catheter by means of complementary gripping sections. Tissue-ingrowth material is affixed to the outwardly facing surface of the cuff within a subcutaneous tunnel after catheter implantation, thus anchoring the catheter against movement.

The cuff described in the cited document has the advantage of being able to be positioned where desired by the surgeon. However, the anchoring of the cuff is entrusted only to the tissue ingrowth around it.

SUMMARY OF THE INVENTION

An object of the present invention is to avoid a displacement of the catheter connected to the external end device from the position in the subcutaneous tunnel where it was installed by the surgeon.

The object is achieved by an external end device equipped with a tissue-ingrowth cuff, as defined in the attached claims.

Advantageously, the cuff according to the invention comprises two distinct bands of Dacron and not only one.

The width of the Dacron bands is considerable compared to that of the catheters on the market today. This already greatly increases, as is easily understood, the mechanical grip of the cuff itself.

From a biological point of view, it is clear that this considerable width also generates an increased barrier to the progression of bacteria which, therefore, have to travel a long road to be able to overcome it and reach the part of the catheter immersed in the blood.

Between the two bands there is a rigid polysulfone ring that is equipped, at the bottom, with two small protrusions in the shape of hooks, oriented at 45°. The two small protrusions, at the moment of implantation, thanks to a simple and light pressure exercised from the outside on them, are anchored to the underlying muscle band: this strengthens and stabilizes the mechanical grip of the cuff itself.

BRIEF DESCRIPTION OF DRAWINGS

Further features and advantages will become most evident in the present description of a preferred but not exclusive embodiment of an external end device, illustrated by way of non-limiting example with the aid of the attached drawings in which:

FIG. 3 shows a side view of the device in FIG. 1;

FIG. 4 shows a top plan view of the device in FIG. 1, without covering element and closing lid.

DESCRIPTION OF A PREFERRED EMBODIMENT OF THE INVENTION

Figure 1:
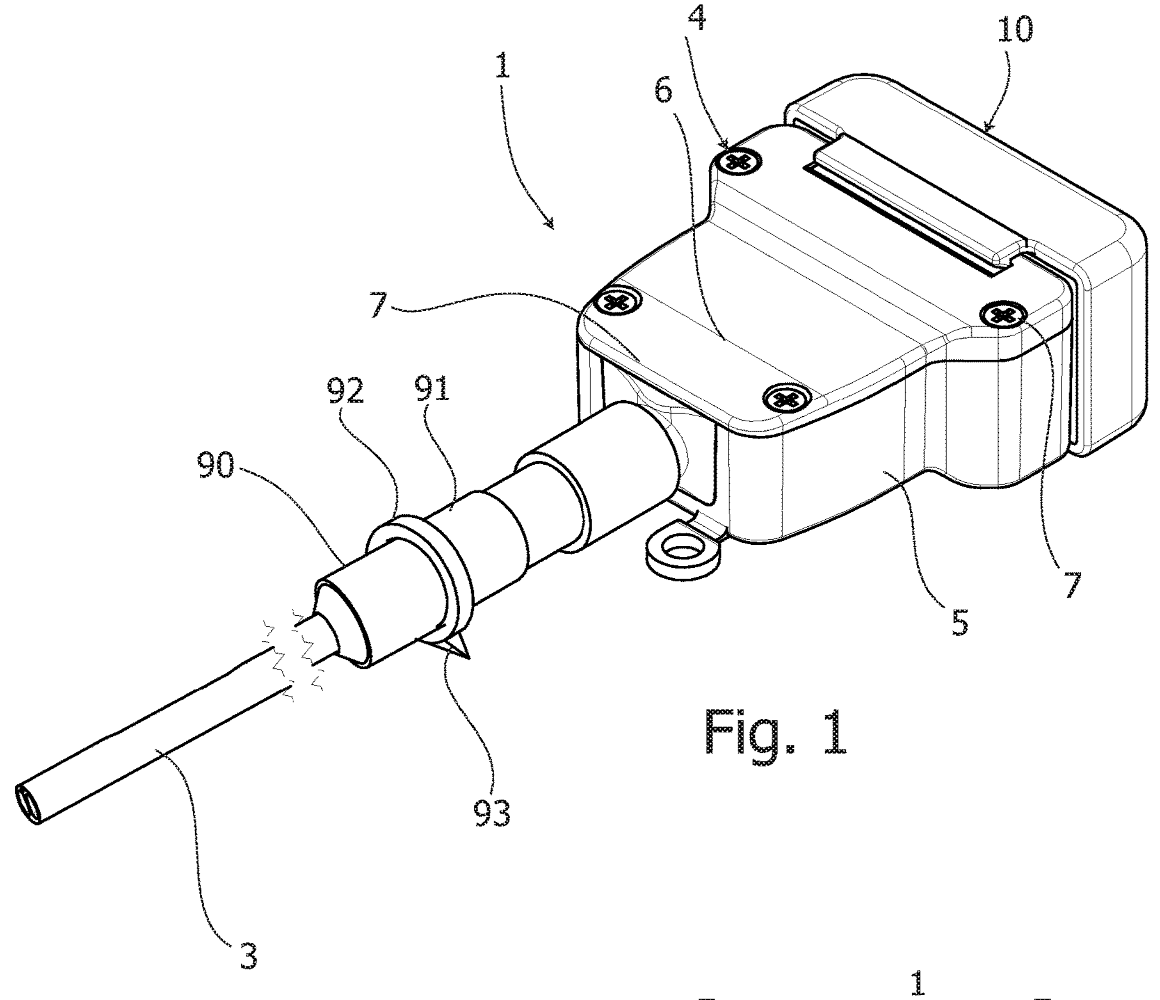
FIG. 1 shows an overall perspective view of an embodiment of the device according to the invention, in the closed position.

Reference is made to FIG. 1, which is a general axonometric view of an embodiment of the external end device according to the invention, in closed position, i.e. not connected to the flow lines of a blood treatment machine. The external end device, generally indicated as 1, is joined to a two-lumen catheter implanted in a patient. As will be explained in detail below, the catheter, indicated as 3, is able to pass through a tubular coating 2 adapted to anchor the end device external to the patient.

Figure 2:
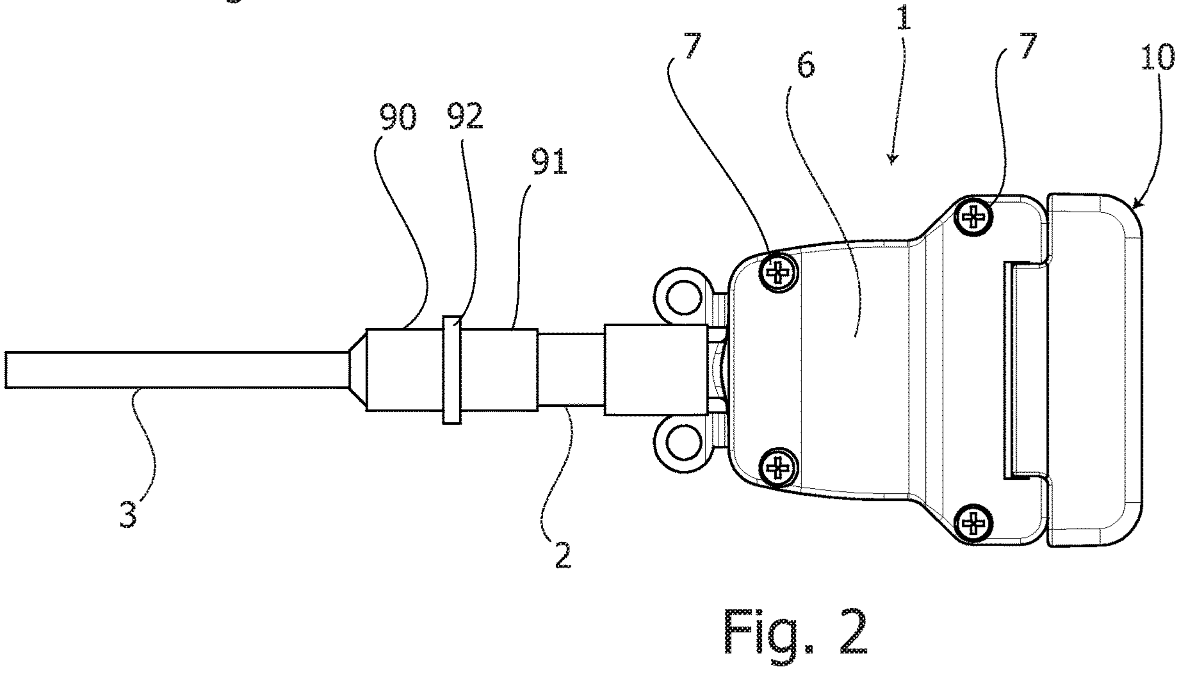
FIG. 2 shows a top plan view of the device in FIG. 1.

Referring also to FIGS. 2 to 4, which show a top plan view, a side view, and a distal end view, respectively, of the external end device 1 in FIG. 1, the external end device 1 comprises a casing 4, including a base 5 and a removable cover 6, fixed with screws, generally indicated as 7, to the base 5. Integrated in the base 5 are two rings 8 useful for sewing the external end device 1 to the patient's skin. The casing 4 is closed by a lid 10.

Figure 5:
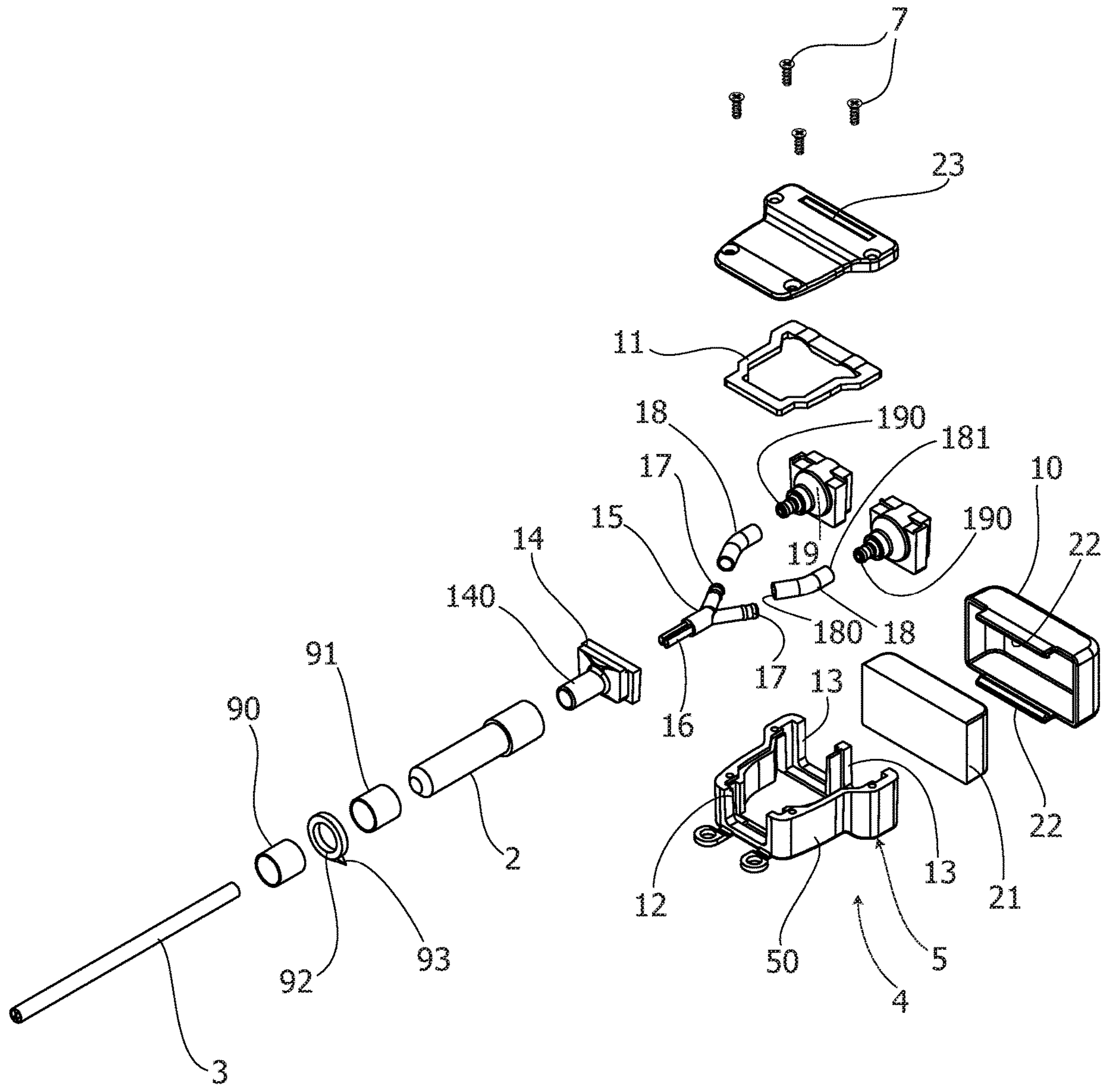
FIG. 5 is an exploded perspective view of the device in FIG. 1.

Referring also to FIG. 5, which is an exploded perspective view of the external end device 1, the casing 4 is shown as closed by the lid 10 with the interposition of an antiseptic sponge 21. The lid 10 has distal projections 22, 22, whose ends engage a corresponding recess indicated as 23 in the removable cover 6 and a similar recess (not shown) created externally in the bottom wall of the base 5 of the casing 4.

The base 5 has side walls 50 on which the removable cover 6 is fixed by means of the screws 7 with the interposition of a gasket 11. The base 5 has a distal opening 12, with respect to the flow lines of a treatment equipment for hemodialysis (not shown), and a pair of proximal openings 13, 13.

The distal opening 12 and the proximal openings 13, 13 are delimited on three sides by grooves adapted to form guides for the insertion of septa. In particular, as shown in FIG. 5, the distal opening 12 provides for the insertion of a septum 14, as will be seen below.

A fitting 15, housed in the casing 4, has a distal tract 16, which engages the catheter 3, and two proximal tracts 17, 17. Each tube of a pair of curved tubes 18, 18 has a distal end 180 which is inserted on the respective proximal tract 17 of the fitting 15, and a proximal end 181. A pair of nozzles 190, 190 is inserted into the proximal end 181, 181 of the curved tubes 18, 18. The distal opening 12 receives a funnel-shaped septum 14 comprising a tube trunk 140 inside which the catheter 3 is connected to the distal tract 16 of the fitting 15. The tubular coating 2 has a proximal end able to be grafted onto the tube trunk 140, and a distal end coaxially adhering to the catheter 3. A pair of bands 90, 91 of tissue-ingrowth material is fixed on the tubular coating 2, and an anchor ring 92, equipped with anchoring means, is sandwiched between the bands 90, 91.

The anchoring means consist of two pointed projections 93, 93, preferably hook-like, facing outwards from the ring 92. The pointed projections 93, 93 are advantageously angled with respect to each other by 45° and facing the opposite site with respect to the patient's skin. Preferably, the bands 90, 91, more than 1 cm wide, are made of Dacron, that is, polyethylene terephthalate, while the anchor ring 92 is made of polysulfone.

Through the tube trunk 140 of the septum 14 passes the catheter 3 to be hooked to the fitting 15 which is located inside the base 5. The distal tract 16 of the fitting 15 is generally a two-lumen catheter portion which is inserted into the catheter 3. The two proximal tracts 17, 17 of the fitting 15 are inserted into the distal end 180 of the curved tubes 18, 18. In the proximal end 181 of the curved tubes 18, 18 are inserted the nozzles 190, 190 received in through septa 19, 19 intended to be retained in the proximal openings 13, 13 of the walls 50 of the casing 4.

The invention claimed is:

1. An external end device equipped with a tissue-ingrowth cuff, the external end device being adapted to be connected, on one side, to a catheter, and, on the other side, to a lid, or alternatively to flow lines of a treatment apparatus, the external end device comprising:

a casing, including a base, a plurality of side walls provided with a distal opening and a pair of proximal openings with respect to said flow lines, and a removable cover on the side walls, a fitting housed in the casing and having a distal tract configured to engage with the catheter, and two proximal tracts, a pair of curved pipes each having a distal end inserted on the respective proximal tract of the fitting, and a proximal end, and a pair of nozzles inserted in the proximal end of the curved tubes, wherein said distal opening of the casing receiving a funnel septum comprising a tube trunk, the catheter being configured to be connected to the distal tract of the fitting inside the tube trunk, a tubular coating having a proximal end configured to be inserted on the tube trunk and a distal end coaxially adherent to the catheter, wherein the external end device further comprises:

a pair of bands of tissue-ingrowth material attached on the tubular coating, and an anchor ring, equipped with projections, sandwiched between the bands.

2. The device according to claim 1, wherein the projections consist of two hook pointed protrusions facing outwards from the ring.

3. The device according to claim 2, in which the hook pointed projections are angled from each other by 45°.

4. The device according to claim 1, wherein the bands are made of polyethylene terephthalate.

5. The device according to claim 1, wherein each band of the pair of bands has a width greater than 1 cm.

6. The device according to claim 1, wherein the anchor ring is made of polysulfone.

* * * * *